Figure 1:
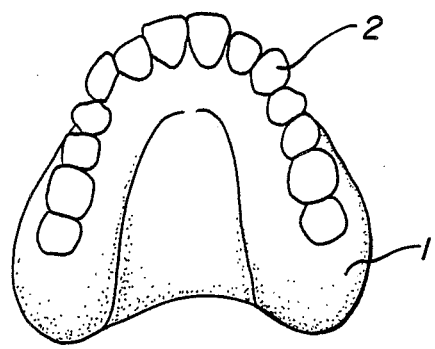

United States Patent [19]

Tatemoto et al.

[11] Patent Number: 4,826,435
[45] Date of Patent: May 2, 1989

[54] DENTURE BASE

[75] Inventors: Masayoshi Tatemoto, Ibaraki; Toshiharu Yagi, Takarazuka, both of Japan

[73] Assignee: Daikin Industries Ltd., Osaka, Japan

[21] Appl. No.: 115,402

[22] Filed: Nov. 2, 1987

[30] Foreign Application Priority Data

Nov. 5, 1986 [JP] Japan .................. 61-170586[U]

[51] Int. Cl.⁴ .................................... A61C 13/01
[52] U.S. Cl. .................... 433/199.1; 106/35; 433/168.1; 433/171; 427/2; 522/141; 523/120
[58] Field of Search ............ 106/35; 433/168.1, 171, 433/199.1, 201.1, 202.1, 212.1; 427/2; 523/118, 120; 522/141, 135, 276

[56] References Cited

U.S. PATENT DOCUMENTS

| | | | |
|---|---|---|---|
| 4,158,678 | 6/1979 | Tatemoto et al. | 525/276 |
| 4,251,215 | 2/1981 | May et al. | 106/35 |
| 4,432,730 | 2/1984 | Gettleman et al. | 433/171 |
| 4,484,894 | 11/1984 | Masuhara et al. | 433/168.1 |
| 4,580,981 | 4/1986 | Bannai et al. | 433/168.1 |
| 4,661,065 | 4/1987 | Gettleman et al. | 433/168.1 |

FOREIGN PATENT DOCUMENTS

| | | | |
|---|---|---|---|
| 0149924 | 7/1985 | European Pat. Off. | 523/120 |
| 2114142 | 8/1983 | United Kingdom | 523/120 |

Primary Examiner—Paul Lieberman
Assistant Examiner—L. Skaling
Attorney, Agent, or Firm—Armstrong, Nikaido, Marmelstein & Kubovcik

[57] ABSTRACT

A denture base at least a part of which comprises a thermoplastic fluoroelastomer exhibits excellent characteristics as a denture base and particularly as a relining material for a denture base.

1 Claim, 1 Drawing Sheet

DENTURE BASE

The present invention relates to a denture base at least a part of which comprises a thermoplastic fluoroelastomer.

The denture base functions, as a base of an artificial tooth, to cover mucous membrane surface, maintain an artificial tooth in oral cavity, hold an artical tooth and transmit biting pressure to mucous membrane. Although denture bases are formerly prepared from wood, natural rubber, celluloid, etc., it is, at the present time, prepared from synthetic resin or metal. The materials for these denture bases require the following characteristics.

(1) The material should have no taste, no odor, no toxicity and no stimulus to a body.

(2) The material should duplicate tissues in oral cavity aesthetically, namely should be freely colored.

(3) The material should not change in color for a long period of use and should have an excellent dimensional stability.

(4) The material should not dissolve in saliva, food or beverage, and the food should not adhere thereto.

(5) The material should have mechanical strength sufficient to use.

(6) The material should be small in specific gravity and have excellent thermal conductivity.

(7) The denture base prepared from the material can easily be mended, etc.

An object of the present invention is to provide a denture base having the above characteristics required for denture base.

The above and other objects of the present invention will become apparent from the following description.

The present invention provides a denture base at least a part of which comprises a thermoplastic fluoroelastomer.

The term 'thermoplastic fluoroelastomer' herein used is intended to mean a fluoroelastomer which shows elasticity like a cross-linked elastomer at a comparatively low temperature (for example, at around room temperature) and shows plastic flow when heated.

Preferably the thermoplastic fluoroelastomer comprises a polymeric chain comprising at least one elastomeric polymer segment and at least one non-elastometic polymer sgement, at least one of these segments being a fluorine-containing polymer segment. Preferably, the weight ratio of the elastomeric polymer segment and the non-elastomeric polymer segment is from 40:60 to 95:5.

More preferred thermoplastic fluoroelastomer comprises a polymeric chain comprising two or three polymer segments, at least one iodine atom liberated from an iodinated compound and bonded to a terminal carbon atom of the polymeric chain and a fragment of the iodinated compound excluding said liberated iodine atom therefrom;

one polymer segment (when the polymeric chain comprises two polymer segments) or one or two polymer segments (when the polymeric chain comprises three polymer segments) being elastomeric polymer segment(s) having a molecular weight of from 30,000 to 1,200,000 selected from the group consisting of (1) a vinylidene fluoride/hexafluoropropylene or pentafluoropropylene/tetrafluoroethylene polymer in a molar ratio of $45\sim90:5\sim50:0\sim35$ and (2) a perfluoro($C_1C_3$-alkyl vinyl ether)(including those having plural ether linkages, the same as hereinafter)/tetrafluoroethylene/vinylidene fluoride polymer in a molar ratio of $15\sim75:0\sim85:0\sim85$, other polymer segment(s) being a non-elastomeric polymer having a molecular weight of from 3,000 to 400,000 selected from the group consisting of (3) a vinylidene fluoride/tetrafluoroethylene polymer in a molar ratio of $0\sim100:0\sim100$ and (4) an ethylene/tetrafluoroethylene/hexafluoropropylene, 3,3,3-trifluoropropylene-1, 2-trifuloromethyl-3,3,3-trifluoropropylene-1 or perfluoro($C_1C_3$-alkyl vinyl ether) polymer in a molar ratio of $40\sim60:60\sim40:0\sim30$, and the weight ratio of the elastomeric polymer segment and the non-elastomeric polymer segment being from $40\sim95:5\sim60$.

The above described preferred thermoplastic fluoroelastomer is disclosed in Japanese Examined Patent Publication No. 4728/1983 and U.S. Pat. No. 4,158,678.

The thermoplastic fluoroelastomer comprises the polymeric chain comprises at least two polymer segments, at least one iodine atom which is liberated from the iodinated compound and bonded to one terminal carbon atom of the polymeric chain and the fragment of the iodinated compound excluding the liberated iodine atom therefrom. The thermoplastic fluoroelastomer may be represented by the formula $$Q[(A-B)I]_n$$

wherein Q is the fragment of the iodinated compound excluding the liberated iodine atom therefrom, A, B, etc. are each a polymer segment provided that at least one of them is a fluorine-containing polymer segment, I is an iodine atom liberated from the iodinated compound, and n is the valency of the fragment Q.

In said thermoplastic fluoroelastomer, at least two polymer segments adjacent each other consist of different monomers or of same monomers in different proportions, provided that at least one of them is a fluorine-containing polymer segment, and at least one of them is a hard segment and at least one of them is soft segment. Preferably, each polymer segment has a molecular weight of at least 3,000 and at least one segment has a molecular weight of at least 30,000, so that telomeric molecular weight range is excluded. Further, when the iodinated compound has a polymerizable double bond in the molecule, the fragment of the iodinated compound excluding the liberated iodine atom therefrom may have such a substituent as is derived from the monomer constituting the polymer segment or the iodinated compound itself. The thermoplastic fluoroelastomer may contain 0.001 to 10% by weight of iodine atom. The iodine atom bonded to the thermoplastic fluoroelastomer can be eliminated by an appropriate treatment or substituted by another atom or a substituent. Such an iodine atom-eliminated or substituted fluoroelastomer is also used in the present invention.

The theromplastic fluoroelastomer can be cured by merely cooling thereof without use of a cross-linking agent, which is different from the case of conventional fluorinated elastomers. Thus, it is unnecessary to add a cross-linking agent and other additives. However, the thermoplastic fluoroelastomer may be cross-linked as desired. Examples of cross-linking agents are organic peroxide compounds, polyhydroxy compounds/cross-linking accelerators, polyamine compounds and like cross-linking agents which are used for conventional fluorinated elastomers. Further, usual additives such as carbon black, silica, talc, etc. may be used. The thermoplastic fluoroelastomer can be cross-linked by known methods, for example, by use of peroxide compound, polyol, polyamine, etc. Further, the present fluoroelastomer can be cross-linked by light or heat, with addition of light-sensitive or heat-sensitive compound. Further, the cross-linking of the fluoroelastomer may be effected by radiation.

When the cross-linking of the fluoroelastomer is effected by use of the organic peroxide compound or by radiation, a polyfunctional compound is preferably added in the fluoroelastomer. Examples of the polyfunctional compounds are those having as the functional group at least one of $CH_2=CH-$, $CH_2=CH-CH_2-$ and $CF_2=CH-$.

Further, inactive fillers may be added to the fluoroelastomer for coloring.

The present thermoplastic fluoroelastomer has high resistances to various inorganic acids, organic acids, alkali, alcohols, etc., and also is excellent in resistances to water and degradation in body. Specific examples of the present thermoplastic fluoroelastomers are Dai-el thermoplastic T-530, T-630 (product of Daikin Industries Ltd.), etc.

The denture base of the present invention can be prepared in the conventional method with the exception of using the above thermoplastic fluoroelastomer as the material for the denture base.

FIG. 1 shows an example of the present denture base. (1)... denture base, (2)... artificial tooth.

The present thermoplastic fluoroelastomer was checked for hemolysis test, cytotoxicity test and physicochemical test. The results were given below.

(1) Hemolysis test

Into 60ml of physiological saline was placed 30g of Dai-el thermoplastic T-530 at 260° F. for 60 minutes. To a specific quantity of the extract was added erythrocytes to obtain 0.5% solution in which erythrocytes floated and the solution was allowed to stand at 37°C. for 48 hours. To the supernatant was added physiological saline and the absorbance of the solution was measured at 520nm to calculate hemolysis percent. Homolysis was up to 2% and it was considered non-hemolytic.

Dai-el thermoplastic T-630 was checked for hemolysis test in the same manner as above but the material was non-hemolytic.

(2) Cytotoxicity test

A sheet having a surface area of 60cm$^2$ was prepared from Dai-el thermoplastic T-530. The sheet was placed into 20ml of Eagle's Minimum Essential Medium (MEM) at 38°C. for 24 hours for extraction. To the extract was added L929 Mouse fibroblast and the mixture was cultured at 38°C. for 24, 48 and 72 hours. The results showed no toxicity, no change in cell structure and no cell lysis in all cases.

Dai-el thermoplastic T-630 was checked for cytotoxicity test in the same manner as above but no toxicity was recognized.

(3) Physico-chemical test

A sheet having a surface area of 450cm$^2$ was prepared from Dai-el thermoplastic T-530. The sheet was placed into 100ml of distilled water at 70°C. for 24 hours for extraction. The extract was 1.29mg in non-volatile residue, 0.18mg in residue on ignition and up to 0.00002% in heavy metal content.

Dai-el thermoplastic T-630 was checked for extraction test in the same manner as above and the extract was 0.23mg in non-volatile residue, 0.33mg in residue on ignition and up to 0.00002% in heavy metal content.

From the above hemolysis test, cytotoxicity test and physico-chemical test, it is considered the present thermoplastic fluoroelastomer has no problem in safety as a medical material.

The denture base of the present invention possesses all of the above-mentioned requirements for the denture base. The present thermoplastic fluoroelastomer has sufficient elasticity and can be molded to a denture base without the addition of a filler, cross-linking agent, cross-linking accelerator, etc. Thus, the denture base of the present invention does not elute a substance which is harmful to the body and gives no physiological damage. Further, the present thermoplastic fluoroelastomer is transparent, can easily be colored in skin-color, excellent in weather resistance and hardly wears. Moreover, the present thermoplastic fluoroelastomer can possess the desired flexibility and modulus of elasticity by controlling the proportions of the polymer segments. The present fluoroelastomer adheres firmly to plane surface when the non-elastomeric polymer segment is low in the proportions. The present thermoplastic fluoroelastomer exhibits excellent characteristics as a denture base and particularly as a relining material for a denture base.

We claim:

1. In a denture base, the improvement comprising forming at least a part of said base from a thermoplastic fluoroelastomer, said thermoplastic fluoroelastomer being a block copolymer comprising two or three polymer segments, an iodine atom liberated from an iodinated compound bonded at a terminal position of said segment and a fragment of the iodinated compound from which at least one iodine atom has been removed bonded at another terminal position of said segment, comprising:

(a) at least one segment being an elastomeric polymer segment having a molecular weight of from 30,000 to 1,200,000, selected from the group consisting of (1) a vinylidene fluoride, hexafluoropropylene or pentafluoropropylene and tetrafluoroethylene in a molar ratio of 45–90:5–50:0–35 and a (2) a perfluoro ($C_1$–$C_3$-alkyl vinyl ether), tetrafluoroethylene and vinylidene fluoride in a molar ratio of 15–75:0–85:0–85; and (b) a second polymer segment being a non-elastomeric polymer having a molecular weight of from 3,000 to 400,000, selected from the group consisting of (3) a vinylidene fluoride and tetrafluoroethylene polymer in a molar ratio of 0–100:0–100 and (4) an ethylene, tetrafluoroethylene, hexafluoropropylene and 3,3,3-trifluoropropylene-1,2-trifluoromethyl-3,3,3-trifluoropropylene-1 or perfluoro ($C_1$–$C_3$-alkyl vinyl ether) polymer in a molar ratio of 40–60:60–40:0–30;

wherein the weight ratio of said elastomeric polymer segment and said non-elastomeric polymer segment is 40–95:5–60.

* * * * *